(12) United States Patent
Utterberg et al.

(10) Patent No.: US 8,641,684 B2
(45) Date of Patent: Feb. 4, 2014

(54) CLOSURE FOR TUBULAR ACCESS PORT

(75) Inventors: David S. Utterberg, Seattle, WA (US); William J. Schnell, Libertyville, IL (US)

(73) Assignee: Nxstage Medical, Inc., Lawrence, MA (US)

( * ) Notice: Subject to any disclaimer, the term of this patent is extended or adjusted under 35 U.S.C. 154(b) by 1312 days.

(21) Appl. No.: 11/247,931

(22) Filed: Oct. 11, 2005

(65) Prior Publication Data

US 2007/0093762 A1    Apr. 26, 2007

(51) Int. Cl.
*A61M 35/00* (2006.01)
*A61M 5/14* (2006.01)

(52) U.S. Cl.
USPC .............................................. 604/256; 604/1

(58) Field of Classification Search
USPC .............. 604/1, 167.01–167.04, 167.06, 244, 604/256, 265, 267, 533
See application file for complete search history.

(56) References Cited

U.S. PATENT DOCUMENTS

| | | | |
|---|---|---|---|
| 2,009,744 A | 7/1935 | Pfefferle | |
| 2,961,682 A | 11/1960 | Gabriele et al. | |
| 2,999,260 A | 9/1961 | King | |
| 3,039,938 A | 6/1962 | Charm | |
| 3,103,029 A | 9/1963 | Valles | |
| 3,108,818 A | 10/1963 | Furstenburg | |
| 3,183,543 A | 5/1965 | Worcester | |
| 3,240,326 A | 3/1966 | Miller | |
| 3,450,129 A | 6/1969 | Avery et al. | |
| 3,741,217 A | 6/1973 | Ciarico | |
| 3,903,345 A | 9/1975 | Baker et al. | |
| 3,915,806 A | 10/1975 | Horlach | |
| 3,945,380 A | 3/1976 | Dabney et al. | |
| 4,065,826 A | 1/1978 | Hough | |
| 4,243,035 A | 1/1981 | Barrett | |
| 4,340,052 A | 7/1982 | Dennehey et al. | |
| 4,440,207 A | 4/1984 | Genatempo et al. | |
| 4,446,967 A | 5/1984 | Halkyard | |
| 4,535,819 A * | 8/1985 | Atkinson et al. .............. 137/846 |
| 4,626,664 A | 12/1986 | Grise | |
| 4,725,267 A | 2/1988 | Vaillancourt | |
| 4,778,447 A | 10/1988 | Velde et al. | |

(Continued)

FOREIGN PATENT DOCUMENTS

| | | |
|---|---|---|
| CA | 2547485 | 11/2006 |
| DE | 2554589 | 6/1976 |

(Continued)

OTHER PUBLICATIONS

International Search Report, dated Aug. 16, 2007.

(Continued)

*Primary Examiner* — Kevin C Sirmons
*Assistant Examiner* — Bradley Osinski
(74) *Attorney, Agent, or Firm* — Miles & Stockbridge P.C.; Mark A. Catan

(57) ABSTRACT

A closure for a tubular access port in a medical fluid flow line or other container comprises a removable cap for enclosing and sealing the tubular access port. The cap has a closed end wall. The end wall carries an extending poker to facilitate the pushing of an antiseptic-carrying material into a lumen of the access port. The poker has an outer diameter that is less than the inner diameter of the access port. A method of using the poker is also described.

19 Claims, 5 Drawing Sheets

(56) References Cited

U.S. PATENT DOCUMENTS

| | | | |
|---|---|---|---|
| 4,826,025 | A | 5/1989 | Abiko et al. |
| 4,959,881 | A | 10/1990 | Murray |
| 5,065,783 | A | 11/1991 | Ogle, II |
| 5,088,146 | A | 2/1992 | Smith et al. |
| 5,190,534 | A | 3/1993 | Kendell |
| 5,242,425 | A | 9/1993 | White et al. |
| D342,134 | S | 12/1993 | Mongeon |
| 5,372,429 | A | 12/1994 | Beaver, Jr. et al. |
| 5,385,372 | A | 1/1995 | Utterberg |
| 5,423,440 | A | 6/1995 | Castaneda et al. |
| 5,433,705 | A | 7/1995 | Giebel et al. |
| 5,533,708 | A | 7/1996 | Atkinson et al. |
| 5,554,135 | A | 9/1996 | Menyhay |
| 5,580,530 | A | 12/1996 | Kowatsch et al. |
| 5,616,135 | A | 4/1997 | Thorne et al. |
| 5,694,978 | A | 12/1997 | Heilmann et al. |
| 5,733,503 | A | 3/1998 | Kowatsch et al. |
| 5,795,343 | A | 8/1998 | Yavitz et al. |
| 5,820,955 | A | 10/1998 | Brander |
| 5,951,519 | A * | 9/1999 | Utterberg ............... 604/167.01 |
| 5,964,785 | A | 10/1999 | Desecki et al. |
| 6,045,539 | A | 4/2000 | Menyhay |
| 6,090,066 | A * | 7/2000 | Schnell ........................ 604/86 |
| 6,290,682 | B1 | 9/2001 | Myers |
| 6,423,550 | B1 | 7/2002 | Jenkins et al. |
| 6,428,251 | B1 * | 8/2002 | Steven ........................ 409/131 |
| 6,468,251 | B1 | 10/2002 | Yamanaka et al. |
| 6,602,244 | B2 | 8/2003 | Kavanagh et al. |
| 6,677,258 | B2 | 1/2004 | Carroll et al. |
| 6,679,529 | B2 | 1/2004 | Johnson et al. |
| 6,753,306 | B2 | 6/2004 | Simpson |
| 6,893,428 | B2 | 5/2005 | Willemstyn |
| 6,911,025 | B2 | 6/2005 | Miyahara |
| 7,127,771 | B2 | 10/2006 | McDevitt et al. |
| 7,198,611 | B2 | 4/2007 | Connell et al. |
| 7,214,214 | B2 | 5/2007 | Sudo et al. |
| 7,316,669 | B2 | 1/2008 | Ranalletta |
| 7,682,561 | B2 | 3/2010 | Davis et al. |
| 7,794,675 | B2 | 9/2010 | Lynn |
| 7,867,204 | B2 | 1/2011 | Bartholomew et al. |
| 7,922,701 | B2 | 4/2011 | Buchman |
| 7,932,099 | B2 | 4/2011 | Egan et al. |
| 2002/0183229 | A1 | 12/2002 | Simpson |
| 2002/0197738 | A1 | 12/2002 | Matsumoto et al. |
| 2003/0026729 | A1 | 2/2003 | Wu et al. |
| 2004/0068238 | A1 | 4/2004 | Utterberg et al. |
| 2004/0068239 | A1 | 4/2004 | Utterberg et al. |
| 2004/0230162 | A1 | 11/2004 | Tan |
| 2005/0042240 | A1 | 2/2005 | Utterberg et al. |
| 2005/0115856 | A1 | 6/2005 | Halkyard |
| 2005/0124709 | A1 | 6/2005 | Krueger et al. |
| 2005/0124970 | A1 | 6/2005 | Kunin et al. |
| 2005/0220567 | A1 | 10/2005 | Winker |
| 2006/0030827 | A1 | 2/2006 | Raulerson et al. |
| 2006/0217671 | A1 | 9/2006 | Peppel |
| 2007/0112333 | A1 | 5/2007 | Hoang et al. |
| 2007/0185383 | A1 | 8/2007 | Mulhern et al. |
| 2008/0011310 | A1 | 1/2008 | Anderson et al. |
| 2008/0019889 | A1 | 1/2008 | Rogers et al. |
| 2008/0038167 | A1 | 2/2008 | Lynn |
| 2008/0039803 | A1 | 2/2008 | Lynn |
| 2008/0086091 | A1 | 4/2008 | Anderson et al. |
| 2009/0028750 | A1 | 1/2009 | Ryan |
| 2009/0041619 | A1 | 2/2009 | Cady et al. |
| 2009/0062766 | A1 | 3/2009 | Howlett et al. |
| 2010/0292673 | A1 | 11/2010 | Korogi et al. |

FOREIGN PATENT DOCUMENTS

| | | |
|---|---|---|
| DE | 2554588 | 2/1977 |
| EP | 0621053 | 10/1994 |
| GB | 1517375 | 7/1978 |
| GB | 1596620 | 8/1981 |
| JP | 10035716 A * | 2/1998 |
| JP | 2001-527441 A | 12/2001 |

OTHER PUBLICATIONS

English translation of Office Action issued Dec. 15, 2011, in Japanese Patent Application No. 2008-535631.

Invitation pursuant to Art. 94(3) and Examiner Consultation, issued Apr. 4, 2013, in European Patent Application No. 06825730.2.

Supplementary European Search Report and Search Opinion, issued Jun. 14, 2010, in European Patent Application No. 06825730.2.

* cited by examiner

FIG. 9
FIG. 10
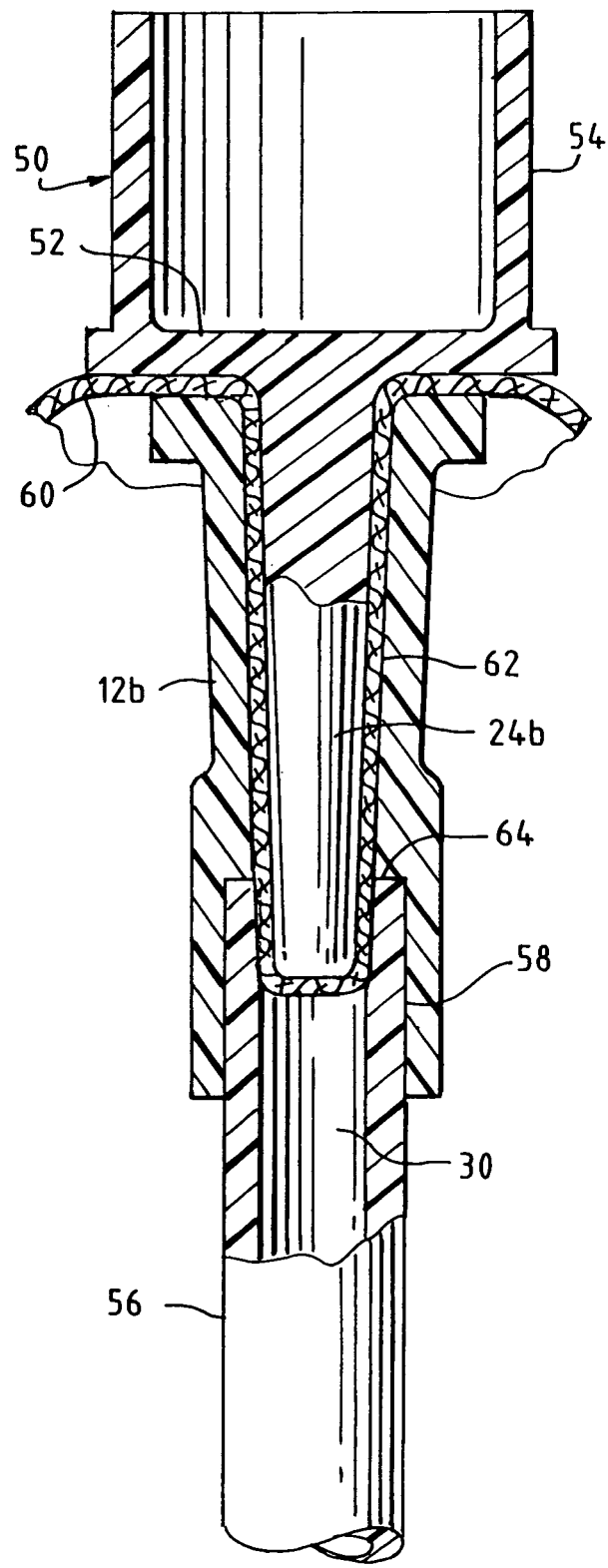
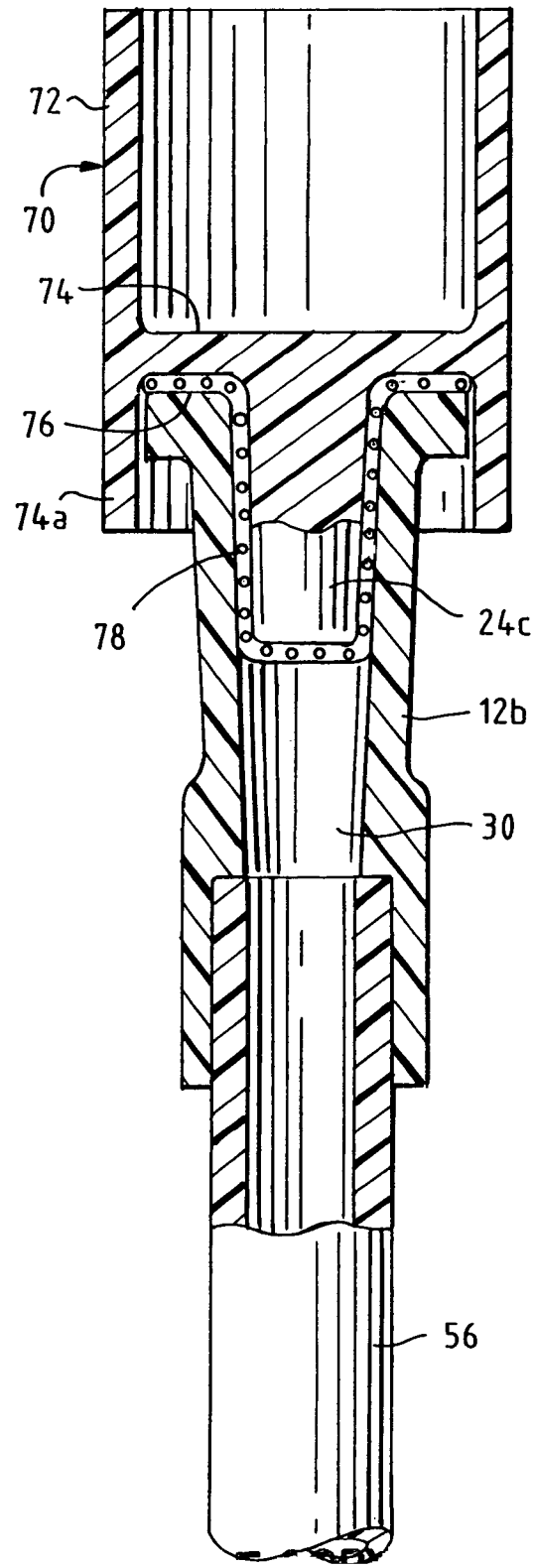

CLOSURE FOR TUBULAR ACCESS PORT

BACKGROUND OF THE INVENTION

Tubular access ports are used in medical fluid flow lines and other medical fluid containers such as blood and parenteral solution bags, syringe chambers for administration of liquids, and various tube sets such as hemodialysis arterial and venous sets, plus other extracorporeal blood flow sets, and parenteral solution administration sets. The tubular portion of the access port is designed to receive a mating connector of another device which fits within the lumen of the tubular portion. To preserve sterility prior to use, the tubular access port may have a closure of conventional design, typically a removable, tubular cap comprising an end wall covering the opening of the lumen, a tubular wall fitting around the outer portion of said tubular portion and, also, typically, a male member attached to the inner face of the end wall that fits down into the lumen of said tubular portion. The tubular access ports themselves may be on the end of a branch tubing which connects to a tube set or other medical fluid container, or the access port may be directly carried on main flow tubing of a branch tubing set, a medical solution bag, a cap of another kind of container such as a dialyzer housing, a drip chamber, or the like.

Specifically, such tubular access ports may comprise a simple, open tubular end having a cylindrical lumen, or it may comprise a female luer or luer lock connector. Also, the tubular access port may be of a design as illustrated in U.S. published patent applications 2004/0068238 or 2004/0068239.

Additionally, such tubular access ports may contain any partial or complete wall which is recessed below the outer end of the port, and which partially or completely blocks or bridges a recessed portion of the lumen of the tubular access port, such as a one-way valve, check valve or a three-way rotary valve and the like.

As a problem with these designs, when the access port is opened, sterility of course is lost in the lumen of the access port and any barriers, valves or mechanisms within the flow pathway of the port, and the port should be resterilized or disinfected if it is to be reused. Typically, only the external portions of tubular and non-tubular access ports, for example, the elastomeric surface and outer housing of resealable elastomeric injection sites for needles are disinfected, typically with a conventional alcohol "prep pad".

In accordance with this invention, a closure is provided for a tubular access port in which disinfection of the lumen of the access port is greatly facilitated at low cost and with great ease, without the need of extra equipment except for, typically, a conventional alcohol "prep pad", or the like, such pads being generally ubiquitous at clinical and medical facilities.

DESCRIPTION OF THE INVENTION

In accordance with this invention, a closure for a tubular access port in a medical fluid flow line or other container comprises: a removable, tubular cap for enclosing the tubular access port. The cap has a closed end wall, with or without a male member attached to its inner face, while typically the end wall's outer face, in turn, carries an outwardly extending poker to facilitate the pushing of an antiseptic-containing material, typically an alcohol "prep pad", into a lumen of the access port to disinfect at least that portion of such lumen that will mate with the connector of a connecting device, for example, a syringe. Preferably, the entire recessed lumen or flow path of the access port receives disinfectant including portions proximal to any barrier or valve mechanisms that are recessed in the lumen and may become contaminated with use. The poker has an outer diameter that is less than the inner diameter of the access port, to provide space in the access port lumen for both the poker and the antiseptic-containing material. The antiseptic containing material may comprise fluid or gelled antiseptics, or antiseptic impregnated materials. Any appropriate antiseptic may be used, such as ethyl or isopropyl alcohol.

To practice this invention in some embodiments, an antiseptic-impregnated material may be placed across or in the open lumen of the access port. This material may comprise, a conventional, alcohol-soaked fabric prep pad, typically isopropanol, but, alternatively, it may comprise a small piece of alcohol-soaked cotton, or other woven or non-woven material. Other antiseptics such as povidone iodine may be used, if desired.

The poker, which generally comprises a small, projecting, semi-rigid or rigid stick of circular cross section (or any other desired cross sectional shape), is inserted into the open lumen of the access port, to force at least a portion of the antiseptic-containing material into the same open lumen to come in contact with the lumen wall, thereby coating such wall with the antiseptic. (If there is a recessed wall within the lumen of the access port that at least partially blocks or bridges the lumen, the poker may preferably be long enough such that this wall is coated with disinfectant material also.) There, the antiseptic-containing material is allowed to reside for a desired period of time, sufficient to provide a chosen antimicrobial effect by either fluid contact or gaseous effect. Thereafter, the antiseptic-containing material and poker may be removed from the open mouth, leaving at least a film of antiseptic remaining in at least the lumen of the access port and the access port is ready for connection in aseptic manner with another connector for the transfer of fluid therethrough.

While occupying the access port, the antiseptic and/or the antiseptic-impregnated material and the poker can provide closure and sealing, preventing ingress of infective materials, as well as delaying evaporation, thereby increasing the persistence of the antiseptic causing antimicrobial effect to any infective materials already in the lumen. As an advantage of the method of this invention, at least the antiseptic-impregnated material, and optionally the poker, may remain in the access port for a substantial period of time prior to removal and use of the access port. In other words, the antiseptic impregnated material and poker can be applied, for example, immediately after disconnection of the initial, sterile connection of a device to the access port. Such persistence of antiseptic within the access port can provide a degree of disinfection which is substantially higher than the conventional exposed swabbing of a site immediately before use by accessing with a needle in that the kill time by this invention can be greatly extended, resulting in a much more reliable disinfection without a change of disinfectant. In other words, isopropyl alcohol may be used, but the level of disinfection is significantly raised by the extended period of exposure of the injection site or the like to the isopropyl alcohol, when compared with disinfection of the site immediately before access is effected, as is now the common practice. Thus, this exposure time to the antiseptic may be minutes and even hours between access events.

Typically, the poker is carried on a cap which is proportioned to cover the access port. This cap may be the original cap that is covering and optionally sealing the access port as it comes from the factory, typically maintaining aseptic conditions within the access port, with the poker extending outwardly from the cap. The same cap may be used to cover and optionally close the access port after the access port has been used, for example by connection with, and then disconnection from, a male luer or other tubular connector. In some embodiments, the poker has a length that is at least approximately the length of the tubular access port, to assure that the antiseptic and/or antiseptic-carrying fabric is driven completely into the access port to engage all of the inner surfaces of the lumen.

The tubular access port may define a female luer shape, and may thus be capable of sealing connection with a male luer or luer lock connector.

Furthermore, in some embodiments, the cap may also define an attached, outwardly extending, typically C-shaped projection which is proportioned to releasably grip a component of a fluid flow set that carries the access port, to releasably attach the cap to the flow set, with the cap being spaced from the access port. Thus, while the access port is in use, for example in a connection with a connector such as a male luer or luer lock connector, the cap may be hung onto medical tubing of the fluid flow set, to retain the cap nearby for convenient, subsequent use. Then, when the connection between the access port and the other connector is broken, the cap may be used as described above to again disinfect the access port, making use of an antiseptic and/or antiseptic-soaked material as described above, typically removing the cap from its connection with the medical tubing, and using the (typically) outwardly projecting poker of the cap to force an antiseptic and/or antiseptic-impregnated material fabric into the lumen of the access port.

Accordingly, by this invention, a multiple use cap is provided which can initially close off an access port and optionally hold it in sterile condition, and the same cap may be used in a simple process to exert antimicrobial effect in the lumen of the access port, while serving as a temporary closure for the access port in conjunction with the antiseptic-carrying material, for a desired period of time to provide the desired antimicrobial effect, and longer if desired. Typically, the cap is positioned backwards, with the poker extending into the access port, until such time as the cap and antiseptic impregnated material may be removed. Then, the cap may be inverted, and may reclose the access port once again in a normal manner.

Additionally, for heightened disinfection, prior to replacing the cap on the disinfected access port, the interior of the cap may first be swabbed with the same or other antiseptic-impregnated material or disinfected by the insertion of antiseptic. Thus the inside of the access port, its external opening, and adjacent locking threads, if any, as well as the inner surfaces of its protective cap may be disinfected before or after each use.

The access port may carry a slit diaphragm or any other partial or full barrier at a recessed point within the access port, examples of this being disclosed in the above cited published patent applications.

The invention also comprises a method of disinfecting an access port of a medical fluid flow line or another container, the access port having an open mouth. The method comprises: inserting at least a portion of a fibrous or spongy, antiseptic-impregnated material, or antiseptic oil or gel on or into the open mouth of an access port with the poker of the above invention to disinfect at least some recessed portions of a tubular access port. Thereafter, the poker and antiseptic material or gel can be removed from the open mouth, when a desired degree of disinfection has been achieved, which may be a matter of minutes and even hours as previously discussed. Alternatively, the antiseptic oil or gel may not need removal.

Examples on how this might be accomplished, as stated above, includes any of the steps of: placing an antiseptic-containing material across the open mouth prior to insertion of the poker; placing an antiseptic-containing material over or around the poker of the cap prior to inserting the poker into the open mouth of the access port; wadding up an antiseptic impregnated fabric or fibrous material such as a cotton ball, and placing it into the lumen of the access port, then using the poker to drive it further inwardly; taking a non-woven fabric or cotton ball impregnated with disinfectant and placing it over the opening, followed by using the poker to drive it in; using an alcohol gel as disclosed in U.S. Patent Publication 2005/0042240 (the disclosures of which are incorporated by reference), or a commercial hand sterilizing gel, and placing it at or into the opening of the access port followed by using the poker to push the antiseptic gel into the port and cover internal surfaces; using the alcohol gel or the like to coat the poker and then inserting the poker into the access port without a fibrous or spongy material present.

Additionally, the interior and/or exterior of the cap which carries the poker may be disinfected before or after disinfecting of the access port, making use of a conventional swab or the like, and then replacing the disinfectant cap on the disinfected access port.

Typically, the fibrous or spongy, antiseptic-impregnated material is a separate item, but such material may be attached to the poker or the like. The antiseptic-impregnated fabric or other material may be placed across or in the open mouth, inserting a poker into the open mouth to force at least a portion of the fabric into the open mouth. Thereafter, the fabric and poker can be removed from the open mouth, when the desired degree of disinfection has been achieved.

DESCRIPTION OF THE DRAWINGS

In the drawings.

FIG. 9 is a longitudinal sectional view of a female luer connector on tubing, with the poker of a sealing cap extending into the female luer, and carrying an antiseptic-soaked fabric surrounding the poker.

FIG. 10 is a longitudinal sectional view of another embodiment of this invention, in which a female luer connector attached to tubing receives an outwardly extending poker of a sealing cap for the connector.

DESCRIPTION OF SPECIFIC EMBODIMENTS

Figure 1:
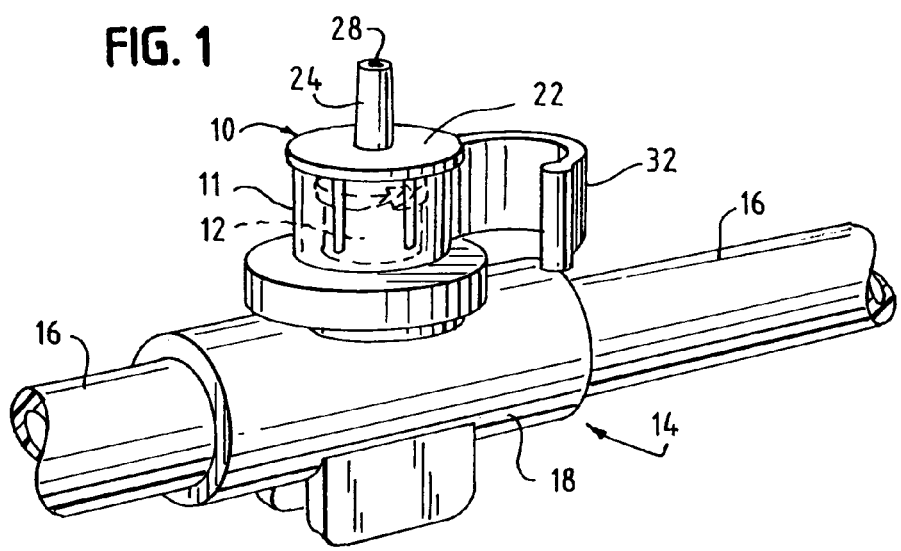
FIG. 1 is a perspective view of a portion of a medical fluid flow line which carries a tubular access port, which is closed by the closure cap of this invention.
Figure 2:
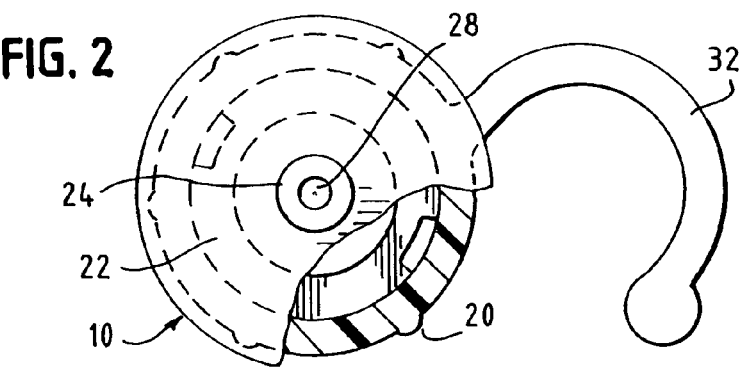
FIG. 2 is a top plan view of the closure cap of FIG. 1, taken partly in section.

Referring to the drawings, a closure 10, in closure cap form for a tubular access port 12 of a medical fluid flow assembly 14 is shown, all being of any known type, but for the novel features of this invention. Medical fluid flow assembly 14 may comprise separate lengths 16 of flexible tubing conventionally sealed into a tubular housing 18, which carries tubular access port 12 having lumen 30 extending through outer end 13 of port 12. Access port 12 (and housing 18) may be of generally conventional design, and is particularly shown to be in the form of a female luer lock connector, having threads 20 or alternatively opposed lugs, to secure a male luer lock connector of another device, for example a syringe, in conventional manner.

Alternatively, closure 10 may be used in conjunction with a corresponding tubular access port that is attached to a solution or blood bag, a drip chamber, a housing, or another kind of medical container. Closure 10 can be seen to define a removable, typically tubular cap for covering tubular access port 12 and optionally sealing lumen 30. Closure cap 10 has a closed end wall 22 and an annular side wall 11 which attaches to the outside of tubular access port 12. Alternatively, attached to end wall 22 is a male member (not shown in FIGS. 1-7) which extends inwardly into and grips at least a portion of the inner lumen of tubular access port 12, or both an annular side wall and male member can be employed to retain closure 10 on access port 12. When the internal male member is absent, as in FIGS. 1-7, the interior 23 of closure 10 can be easily disinfecting-swabbed, being typically large enough for that, permitting reuse.

End wall 22, in turn, can carry an outwardly extending poker 24 (i.e. extending in opposite direction from annular wall 11 or the male member). Poker 24 is shown to be tubular in structure for the saving of material in manufacture, but its lumen 28 typically does not extend through closed end wall 22. Alternatively, poker 24 may be solid, and it also may be of square, triangular, or other cross section if desired, rather than being substantially cylindrical. Also, poker 24 may taper if desired.

Figure 7:
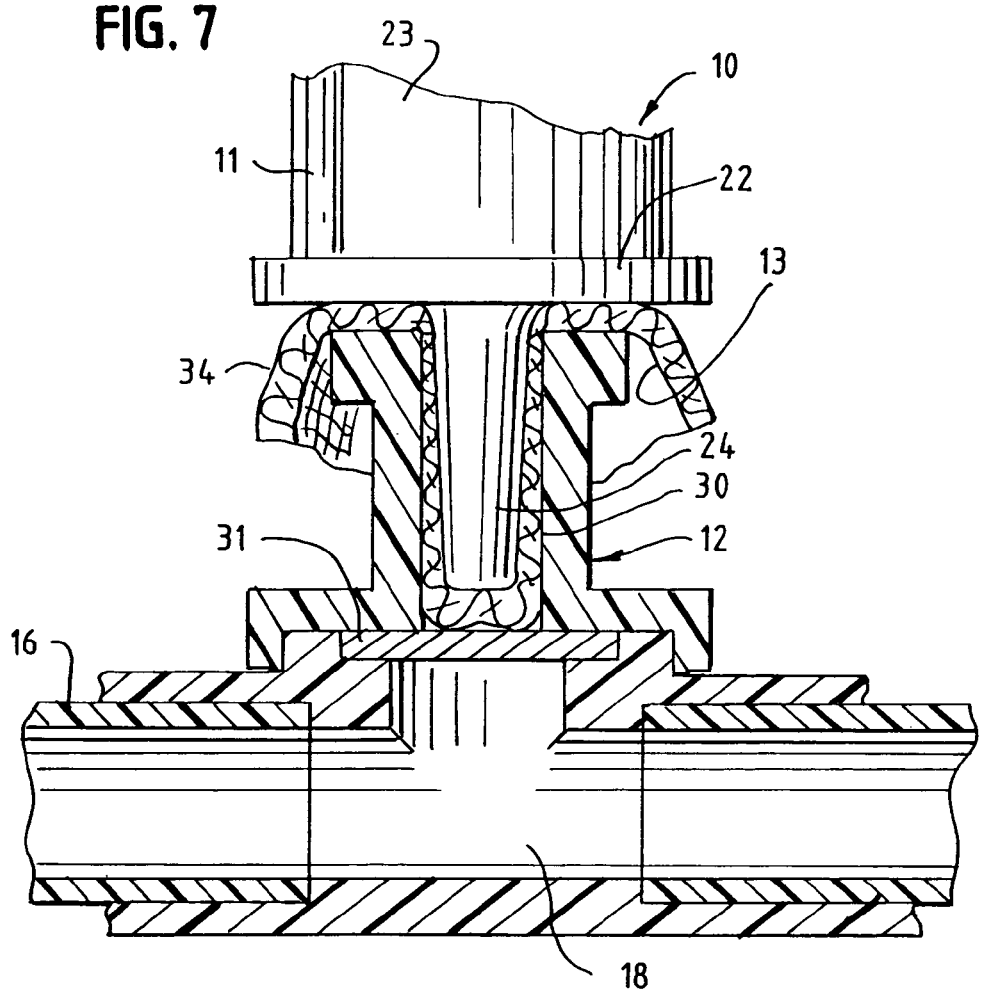
FIG. 7 is an enlarged, fragmentary, sectional view taken along line 7-7 of FIG. 6, with a portion removed.

It can be seen particularly from FIG. 7 that the portion of poker 24 that is inserted into lumen 30 of access port 12 has an outer diameter that is less than the inner diameter of the lumen 30 of access port 12. Also, it can be seen that poker 24 has a length that is approximately or almost the same as the length of lumen 30 of tubular access port 12, extending from outer end 13 to an optional recessed internal, slit, elastomeric barrier wall 31, for example similar to those described in the above cited, published patent applications 2004/0068238 and 2004/0068239 (the disclosures of which are incorporated by reference). In this embodiment, the female lumen 30 of access port 12 has a terminus, i.e. slit elastomeric wall 31. Alternatively, lumen 30 has no nearby terminus, and may comprise a standard female luer on a fistula needle. Here, poker 24 may optionally only be at least as long as the mating length of lumen 30 which is in contact with a connected male luer, so poker 24 and antiseptic or antiseptic-impregnated material can disinfect at least this crucial portion of lumen 30. However, if desired, poker 24 may be much longer than this, and even may swab down into the lumen tubing to which the female luer connector is bonded.

In some embodiments, the poker outer diameter is about 0.1-3 mm. less than the inner diameter of lumen 30, preferably about 0.5 to 2 mm. less.

Figure 3:
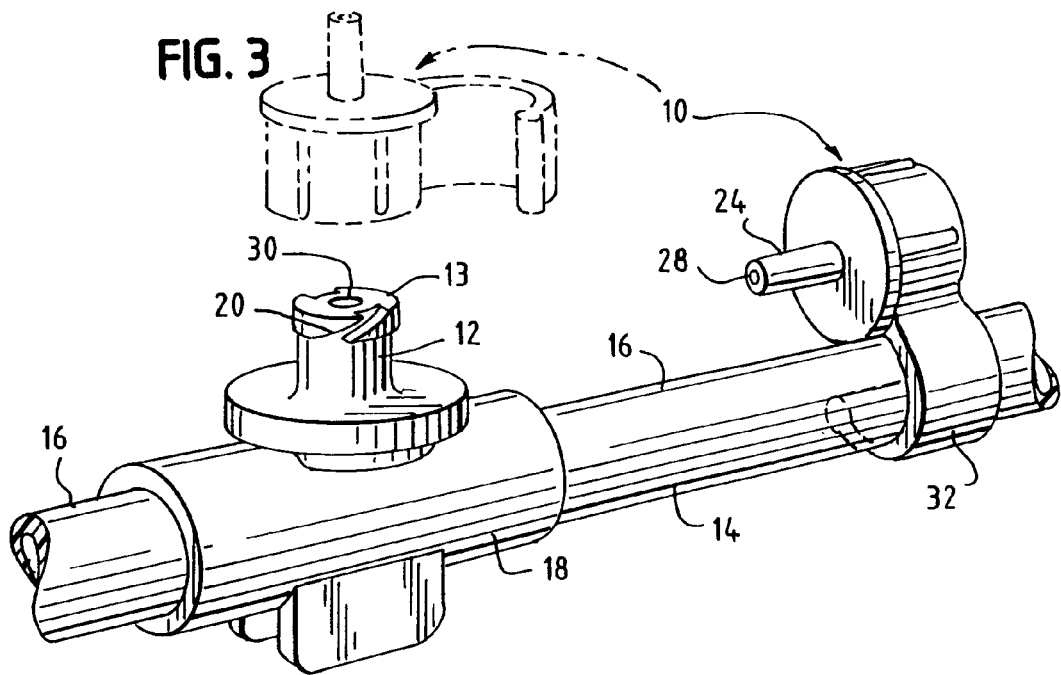
FIG. 3 is a perspective view of the flow tube and access port of FIG. 1 with the cap hanging on the tubing by means of the C-shaped projection.

Furthermore, closure cap 10 defines an attached, outwardly extending, typically C-shaped projection 32, which is proportioned to releasably grip medical tubing 16 of fluid flow set 14, as particularly shown in FIG. 3. Thus, cap 10 can be releasably attached to flow set 14 at tubing 16 thereof, with the cap being spaced from access port 12, as in FIG. 3. This prevents caps 10 from being lost when not in use, for example when access port 12 is in connection with another connector of another medical device. When access port 12 comprises a female luer lock connector, it may thus connect with a male luer or luer lock connector of a flow line from a medical solution bag or a syringe, to provide medication to tubular set 14, or the like.

As shown in FIG. 1, closure cap 10 may initially provide a sterile barrier, by sealing or tortuous pathway, to tubular access port 12, as provided from the manufacturer. When use of the access port is desired, closure cap 10 can be removed, as indicated in FIG. 3, being preferably hung along tubing 16 by the use of C-shaped projection, as shown. Then, a male luer or luer lock connector may be applied to access port 12 in a conventional manner, not shown.

Figure 4:
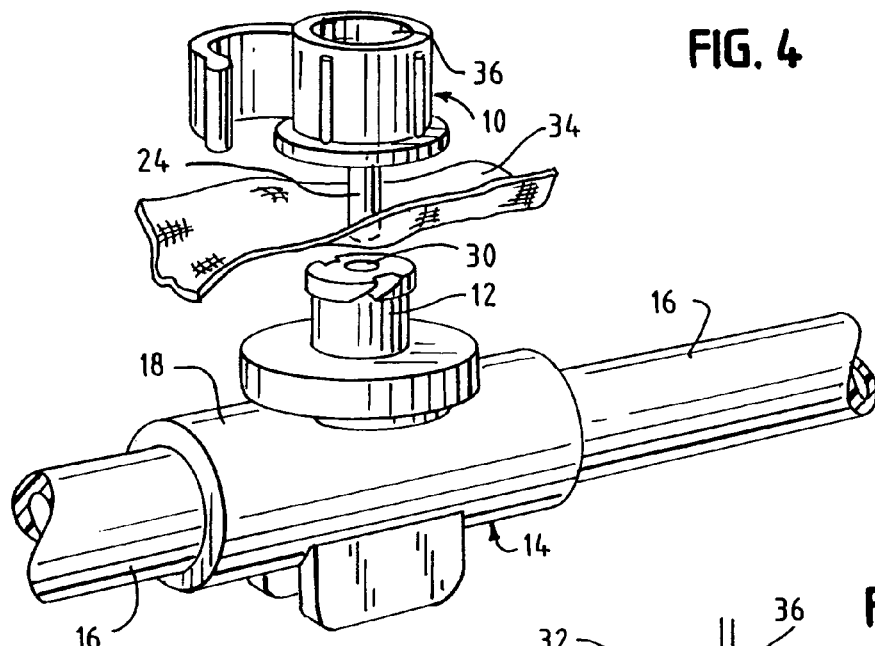
FIG. 4 is a perspective view of the flow tubing and access port of FIG. 1, showing how the lumen of the access port may be covered with an antiseptic-carrying fabric, and with the cap accompanying, in inverted position.
Figure 5:
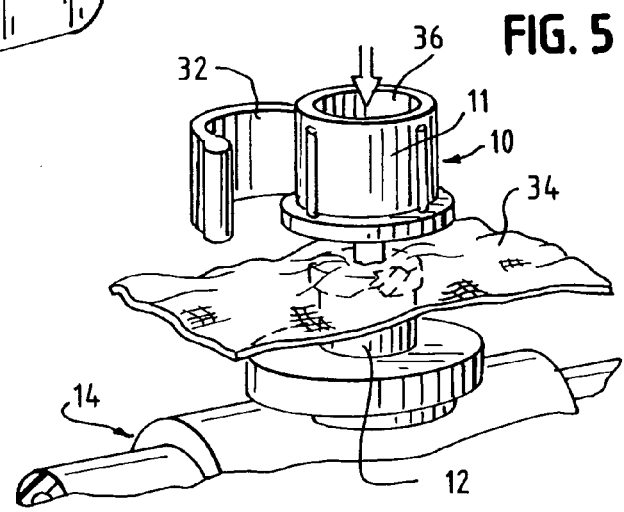
FIG. 5 shows the cap, flow tube and access port of FIG. 4, connected together with the poker driving the antiseptic-carrying fabric into the lumen of the access port.

After the male luer or luer lock connector has been used and then disconnected, a fluid transfer having been made, cap 10 may be placed again on access port 12 in a normal manner. However, if and when it is contemplated that access port 12 might be reused, and that it is desirable for aseptic conditions to be provided once again to access port 12, as shown in FIGS. 4-7 a conventional, alcohol-soaked pad 34 may be placed over the outer end of access port 12, this being one of the examples of inserting of fibrous or spongy, antiseptic-impregnated materials listed above. Closure cap 10 may be removed from its position of FIG. 3, and inverted so that poker 24 points toward access port 12 (FIG. 4). The poker 24 of cap 10 is then advanced into lumen 30 of access port 12 because its diameter is somewhat less than the inner diameter of lumen 30, thus allowing space for both the poker 24 and the material of pad or swab 34 to enter the lumen 30. This has the effect of driving a portion of the alcohol soaked pad 34 into lumen 30, as particularly shown in FIG. 7, with poker 24 pointing inwardly, and open mouth 36 of closure cap 10 pointing outwardly. Since poker 24 has an outer diameter that is less than the inner diameter of lumen 30, alcohol soaked pad 34 is urged into lumen 30, as shown in FIG. 7, as poker 24 is pressed into lumen 30.

Figure 6:
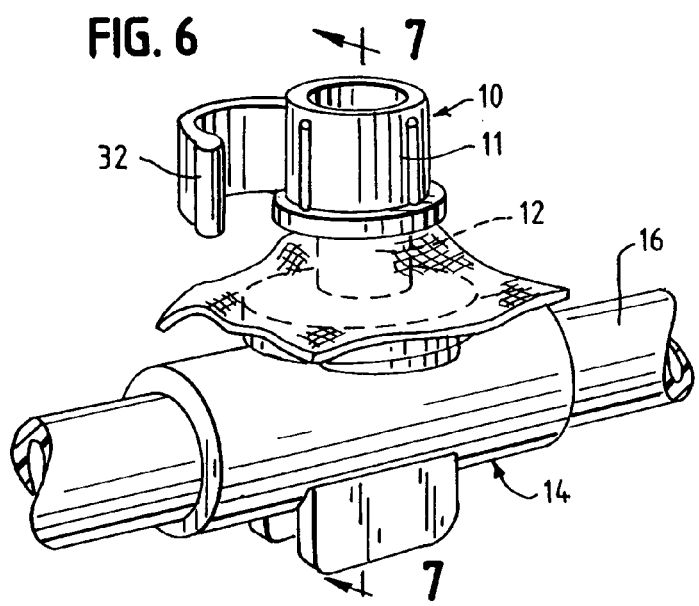
FIG. 6 is a perspective view of access port at FIG. 5, showing the access port lumen being filled with antiseptic-containing fabric, driven in by the poker of the closure cap, to provide antimicrobial effect in the bore.

Cap 10 and antiseptic impregnated pad 34 may be retained in their access port-closing position shown in FIGS. 6 and 7 for a length of time which is sufficient to assure a high level of disinfection of lumen 30 and at least some outer surfaces of access port 12, typically two minutes or more. Particularly, cap 10 may remain in closing relationship as in FIGS. 6 and 7 for an indeterminate period of time, for example hours, while set 14 is in use, since it provides a sealing function as well as an antimicrobial function.

In some embodiments, lumen 30 of tubular access port 12 may also comprise an inner, slit barrier wall or diaphragm 31 (FIG. 7), so that an internal closure is provided, to restrict the passage of antiseptic into the main flow path of set 14, while still permitting the flow of fluids through the slit of diaphragm wall 31 in either direction when access port 12 is properly connected with a male connecting device which opens such slit such as a male luer. For example, such tubular access ports are disclosed in the previously cited U.S. published patent applications 2004/0068238 and 2004/0068239.

Then, if and when it is desired to reuse access port 12, closure cap 10 and fabric 34 can be removed, presenting an open access port as in FIG. 3, which may then be connected with a conventional connector such as a male luer or luer lock connector while closure cap 10 may preferably be placed on tube 14 by clip 32.

Subsequent to this, access port 12, if desired, may be again treated in the manner described above for antimicrobial effect, making use of the inverted cap closure 10 and poker 24, plus a new antiseptic-carrying fabric 34. Alternatively, access port 12 may be simply reclosed with closure cap 10, to assume once again the configuration of FIG. 1.

Figure 8:
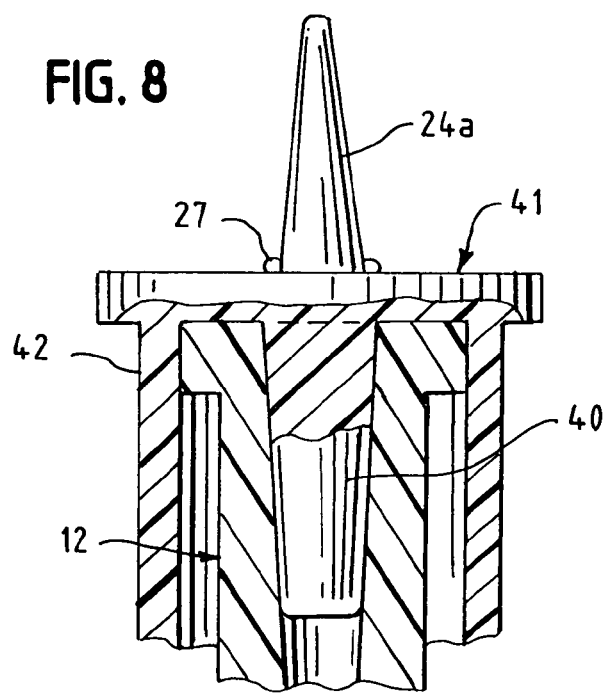
FIG. 8 is a fragmentary sectional view similar to FIG. 7 showing a conventional sealing cap for a female luer in accordance with the prior art, but also carrying a poker in accordance with this invention.

Referring to FIG. 8, a cap 41 is disclosed in which a projecting member 40 extends into lumen 30 of access port 12. It can be seen that, in accordance with the prior art, tapered, luer like projecting member 40 is of substantially the same outer diameter as the diameter of lumen 30 to provide abutting surfaces, with projecting member 40 substantially filling lumen 30 thereby sealing lumen 39 and/or providing retention of the cap to access port 12 with or without annular wall 42.

As a difference between the prior and this present invention, poker 24a, used to insert antiseptic material into lumen 30, is of reduced diameter, to make room for antiseptic-impregnated fabric 34 or other antiseptic material, as shown in FIG. 7. In FIG. 8, poker 24a may extend inwardly, as a replacement for projecting member 40, being of lesser diameter, to create a space in lumen 30 around poker 24a that receives an antiseptic-impregnated fabric, sponge, or gel, in the manner of this invention. In that circumstance, room may have to be allotted between the tubular flange 42 and access port 12 for an excess of antiseptic impregnated fabric 34, or the like.

Alternately, poker 24a may be mounted on an optional, larger diameter base 27 such as an annular ring, to provide frictionally or snap-fit abutting surfaces with an optionally slightly recessed outer portion of lumen 30, for temporary securance of connector 12 and cap 41 together. Such base 27 with surmounted poker 24a may be either outwardly extending or inwardly extending.

Thus, FIG. 8 shows an embodiment of a closure cap in accordance with this invention, having a poker 24a on the cap 41 in a position opposed to projecting member 40, in which poker 24a is of reduced outer diameter relative to projecting member 40, and may be used in a manner similar to that which is disclosed above, by inverting of cap 41, but projecting internal sealing member 40 of cap 41 may be inserted into access port 12 without an intervening, antiseptic-impregnated fabric, in a releasably retained manner.

Referring to FIG. 9, another embodiment of the invention is shown in which closure cap 50 comprises a tubular cap body with a closed end 52 and an attached, tubular cap body wall 54, in a manner similar to the previous embodiments. Cap 50 defines a poker 24b, in a manner similar to previous embodiments, which extends outwardly from wall 52.

As shown in FIG. 9, a connector port 12b comprises a female luer, which is attached to flexible tubing 56 in a conventional manner within a rear recess 58 of female connector 12b.

Cap 50 has been, if desired, previously been carried on female connector 12b in a manner which is inverted from the position shown in FIG. 9, and analogous to that of FIG. 1, in its original configuration, as provided to the user. Then, cap 50 is removed, and female connector 12b is used in conventional manner, typically by connection with a male luer connector. Thereafter, the male luer connector is removed, and cap 50 is applied in the manner shown in FIG. 9, with a piece of antiseptic soaked fabric 60 applied between poker 24b and the inner diameter of lumen 62 of female connector 12b, for antibacterial effect. This permits reuse of the connector at a subsequent time, with an exponentially reduced level of microorganisms remaining therein.

In this embodiment, poker 24b is long enough so that it crosses junction 64 within recess 58 between connector 12b and the flexible, plastic tubing 56 upon which connector 12b is carried, for antimicrobial effect in that area.

Referring to FIG. 10, in another embodiment, cap 70, of broadly similar design to the previously described caps, comprises a tubular cap body 72 having a closed end wall 74. Poker 24c is carried by wall 74, as in previous embodiments, and extends, in this embodiment, for a distance that is substantially the distance through lumen 30 which is in contact with a typical connecting male connector member, such as a male luer, and not substantially farther. This is in contrast with the embodiment of FIG. 9. It can be seen that cap 70 is in connection with the same or a similar female connector 12b as in the previous embodiment.

Also, cap 70 carries an annular, proximally extending wall 74a, which serves to enclose the outer end 76 of female connector 12b in the position shown. Cap 70 can originally be used to close connector 12b in the position that is inverted from that shown in FIG. 10.

In this particular embodiment, the narrow space between poker 24c and the inner diameter wall of lumen 30 may be filled with a fluid antiseptic agent 78, which may have been applied as a coating to poker 24c immediately prior to placement into connector 12b. Such a fluid material may comprise an oil like Betadine, or a gelled alcohol, for example, similar to those of the previously cited published applications, or it may comprise an antiseptic-impregnated fabric which is permanently attached to poker 24c. Alternatively, a fabric like fabric 60 may be used.

Figure 11:
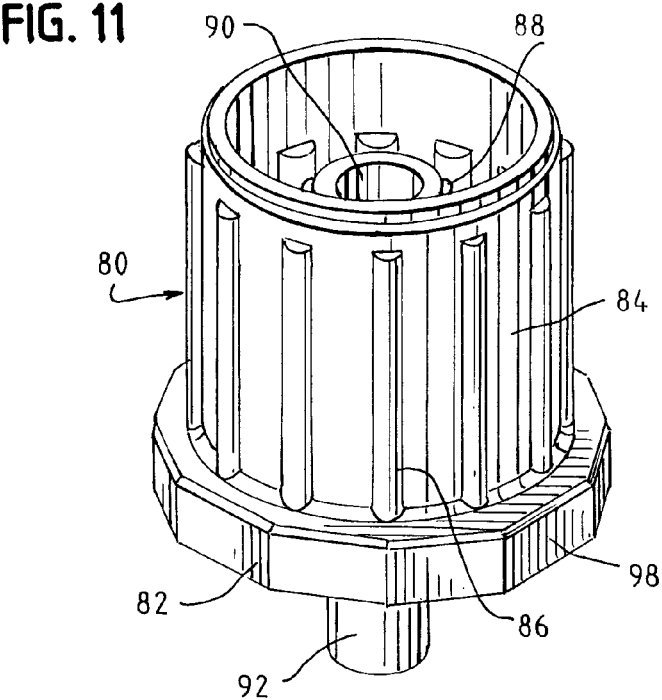
FIG. 11 is a perspective view of another embodiment of the cap of this invention.
Figure 12:
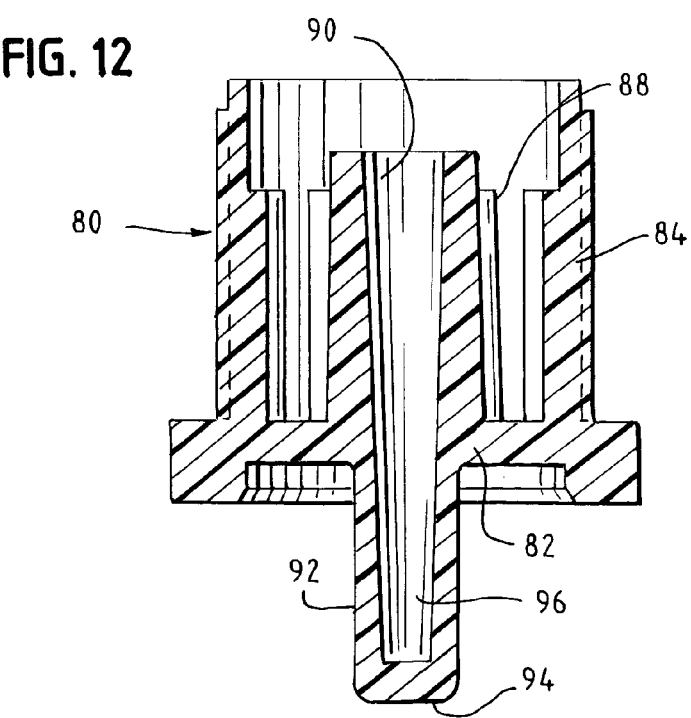
FIG. 12 is a longitudinal sectional view of the cap of FIG. 11.

Referring to FIGS. 11 and 12, another embodiment of the cap of this invention, broadly similar to the cap of FIG. 8, is shown. Cap 80, comprises a tubular cap body with a closed end 82 and an attached, tubular cap body wall 84. Tubular cap body wall 84 defines retention ribs 86 outside of wall 84 and more retention ribs 88 inside of wall of 84. Cap 80 is shown in an inverted condition from its normal use for closing an open end tube. As in previous embodiments, cap 80 may be furnished to the user in closed, sealing relation with an open ended tube for sterile closure or the like. Central tube 90 is provided for improved sealing of such an open ended tube. In this embodiment, central tube 90 has a lumen 96 that extends through closed end wall 82 into an outwardly projecting poker section 92 having a closed end 94, for the purpose of reduction of the amount of material needed in the manufacture of cap 80.

Poker 92 may be used in the manner previously described with respect to other embodiments of the cap of this invention.

Outer ribs 86 and the flat faces 98 of the periphery of closed end wall 82 are used to improve the gripping characteristics of cap 80, the periphery 98 being a polygon as shown.

Accordingly, by this invention, a closure cap is provided which permits the repeated usage of a tubular access port of a medical fluid flow line or other container, where the closure cap remains accessible and not easily lost, and participates in the antimicrobial treatment of the recessed portions of the access port, as desired, between uses of the port.

The above has been offered for illustrative purposes only, and is not intended to limit the scope of the invention of this application, which is as defined in the claims below.

That which is claimed is:

1. A closure kit for a lumen-defining tubular access port of a medical fluid flow line or other container, the closure kit comprising:
   an antiseptic-containing fabric; and
   a removable cap for enclosing and sealing said tubular access port, said cap having a closed end wall, said end wall carrying an extending poker to facilitate the pushing of the antiseptic-containing fabric into a lumen of said access port,
   wherein the poker has an outer diameter that is less than the inner diameter of said access port so as to provide a space therebetween along substantially all of the length of the poker when the poker is fully inserted into said access port,
   the antiseptic-containing fabric being sized and shaped so as to substantially fill said space between the poker and the access port.

2. The closure kit of claim 1 in which said poker has a length that is insufficient to allow said poker to penetrate a barrier wall positioned across said lumen, when said cap is carried with the poker positioned within the tubular access port.

3. The closure kit of claim 2 in which said cap is carried with the poker positioned within the tubular access port.

4. The closure kit of claim 3, wherein the cap is positioned with said poker being surrounded by a portion of the antiseptic-containing fabric which occupies said lumen, the antiseptic-containing fabric comprising an alcohol-soaked pad.

5. The closure kit of claim 1 in which said lumen of the tubular access port defines a female luer shape.

6. The closure kit of claim 1 in which said tubular access port is part of a medical tubing-containing fluid flow set.

7. The closure kit of claim 6 in which said cap defines an attached, outwardly extending projection proportioned and of a stiffness to releasably grip the medical tubing of said fluid flow set along substantially all of the length of said projection, to permit releasable attachment of said cap to the flow set with the cap being spaced from the access port.

8. The closure kit of claim 1 in which said antiseptic-containing fabric comprises an alcohol-soaked pad.

9. The closure kit of claim 1 in which the poker has an outer diameter along its length that is at least 0.5 mm less than the diameter of the access port lumen.

10. The closure kit of claim 9 in which said tubular access port is part of a medical tubing-containing fluid flow set.

11. The closure kit of claim 10 in which said cap defines an attached, outwardly extending, C-shaped projection proportioned and of a stiffness to releasably grip medical tubing of said fluid flow set along substantially all of the length of said projection, to permit releasable attachment of said cap to the flow set with the cap being spaced from the access port, and in which said lumen of the tubular access port defines a female luer shape.

12. The closure kit of claim 1, further comprising:
   a base portion at an end of the poker adjacent to said end wall, said base portion comprising an annular ring with an outer diameter greater than an outer diameter of said poker,
   wherein the annular ring is configured for friction- or snap-fit with a portion of the lumen when the poker occupies said access port so as to retain said cap with said access port.

13. A removable cap for enclosing and sealing an access port of a medical fluid flow line or another container, which cap defines an attached, outwardly extending, C-shaped projection proportioned and of a stiffness to releasably grip medical tubing of said medical fluid flow line along substantially all of the length of said C-shaped projection, to permit releasable attachment of said cap to the flow line with the cap being spaced from the access port.

14. The cap of claim 13, wherein said cap comprises a closed end wall, said end wall carrying an extended poker to facilitate the pushing of an antiseptic-containing material into a lumen of the access port, the poker having an outer diameter that is less than the inner diameter of said access port, to provide a space therebetween along substantially all of the length of the poker when the poker occupies said access port, said space being substantially filled with an antiseptic-containing material, and said poker extends axially outwardly from the remainder of said cap.

15. The cap of claim 14 in which lumen of the tubular access port defines a female luer shape.

16. The cap of claim 14 in which said tubular access port is part of a medical tubing-containing fluid flow set.

17. The cap of claim 14, with said poker penetrating the lumen of a lumen-defining accessing port, said poker being surrounded by said antiseptic-containing material which occupies said lumen.

18. The cap of claim 17 in which said antiseptic-containing material comprises an alcohol-soaked pad.

19. The cap of claim 14 in which the poker has an outer diameter along its length that is at least 0.5 mm less than the diameter of the access port lumen.

* * * * *